US00PP36055P2

(12) United States Plant Patent
Hansen

(10) Patent No.: US PP36,055 P2
(45) Date of Patent: Jul. 30, 2024

(54) ***COREOPSIS* PLANT NAMED 'Heartstrings'**

(50) Latin Name: *Coreopsis verticillata*
Varietal Denomination: Heartstrings

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,663

(22) Filed: Dec. 15, 2023

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./263.1, 417
See application file for complete search history.

*Primary Examiner* — Karen M Redden

(57) ABSTRACT

A new and distinct Threadleaf *Coreopsis* plant, *Coreopsis verticillata* plant named 'Heartstrings', with narrowly-linear, deeply-dissected, 3-lobed, to rarely 6-lobed foliage of bright-green and numerous flowers of rich reddish-raspberry ray florets with cream white edges over a prolonged flowering season from mid-June util late summer. The new plant is useful for landscaping as a specimen plant, en masse, in containers, and as a cut flower.

1 Drawing Sheet

Botanical designation: *Coreopsis verticillata.*
Cultivar denomination: 'Heartstrings'.

STATEMENT REGARDING PRIOR DISCLOSURES UNDER 37 CFR 1.77(b)(6)

The first public disclosure of 'Heartstrings', in the form of a website to the public and email release to customers, was made by Walters Gardens, Inc. on Dec. 1, 2023. Walters Gardens, Inc. obtained the new plant and information about the new plant directly from the inventor. The first offer for sale of the new plant was on Jan.9, 2023, by Walters Gardens, Inc. No plants of *Coreopsis* 'Heartstrings' have been offered for sale or sold in this country or anywhere in the world, nor has any disclosure of the new plant been made, more than one year prior to the filing date of this application, and such sale or disclosure within one year was either derived directly or indirectly from the inventor.

BACKGROUND OF THE PLANT

The present invention relates to the new and distinct Threadleaf *Coreopsis* herein also referred to as *Coreopsis* 'Heartstrings', by the cultivar name, 'Heartstrings', or as the new plant. The new plant was from the cross on Jun. 1, 2017, involving 'Hot Paprika' U.S. Plant Pat. No. 28,522 as the female or seed parent and the plant identified by breeder code 16-22-x (not patented) as the male or pollen parent in the research facility of a wholesale perennial nursery based in Zeeland, MI, USA. The single seedling initially identified by breeder code 17-10-10 was then isolated and compared in subsequent years to other *Coreopsis* and subsequently found to be different from all cultivars known to the discoverer.

Asexual propagation at the same nursery in Zeeland, MI, USA by cuttings has shown 'Heartstrings' to be stable and reproduce true to type in successive generations since spring 2019.

SUMMARY OF THE PLANT

*Coreopsis* 'Heartstrings' has not been observed in all possible environmental conditions. The phenotype may vary slightly with changes in environments such as light intensity, fertility, water availability, etc. without, however, any variation in genotype.

*Coreopsis* 'Heartstrings' is distinct from all cultivars known to the inventor in the following traits:

1. Narrow foliage with compact height and dense habit.
2. Heavy flowering of rich raspberry-reddish ray florets with creamy white edges.
3. Flowers are produced tightly and densely above the bright-green thin foliage.
4. Long flowering period beginning with concentration in mid-June and continuing until late summer.

Plants of *Coreopsis* 'Heartstrings' are most similar to: 'Zesty Zinger' U.S. Plant Pat. No. 29,921, 'Red Hot Vanilla' U.S. Plant Pat. No. 30,909, 'Starlight' U.S. Plant Pat. No. 28,005, 'Berry Chiffon' U.S. Plant Pat. No. 27,414, 'Broad Street' U.S. Plant Pat. No. 24,598, and 'Red Chiffon' U.S. Plant Pat. No. 27,528.

'Zesty Zinger' has ray florets that are cream-colored on the outside and dark magenta in the inside. 'Red Hot Vanilla' has ray florets that are cream-colored on the outside and smaller dark red in the center. 'Starlight' is a *C. grandiflora* hybrid, has simple lanceolate foliage, and the ivory-colored ray florets are longer with dark crimson in the center. 'Berry Chiffon' is a hybrid with ray florets that have a deeper greenish-yellow edge and the center is not as dark reddish. 'Broad Street' has lighter, nearly solid reddish ray florets with just a speckling of the yellow toward the apices. 'Red Chiffon' has ray florets that are brilliant greenish-yellow on the outside and the foliage is less dissected.

The female parent, 'Hot Paprika' has solid reddish ray florets without the creamy white edges. The male parent has ray florets with a burgundy center and a yellowish edge.

BRIEF DESCRIPTION OF THE DRAWINGS

The color drawings illustrate the overall characteristics of *Coreopsis* 'Heartstrings' as three-year-old plants grown in full-sun in Zeeland, Michigan. The colors are as true as reasonably possible given the technology available. The color values may vary slightly depending on light intensity and quality.

DETAILED BOTANICAL DESCRIPTION

Figure 1:
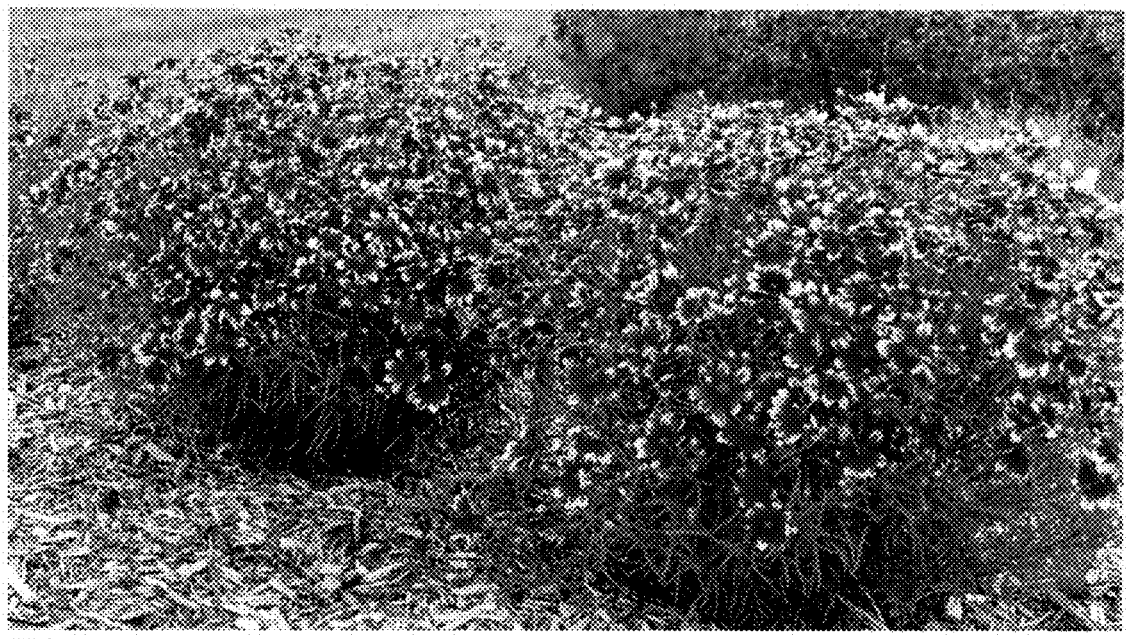
FIG. 1 shows two new plants in a landscape environment.
Figure 2:
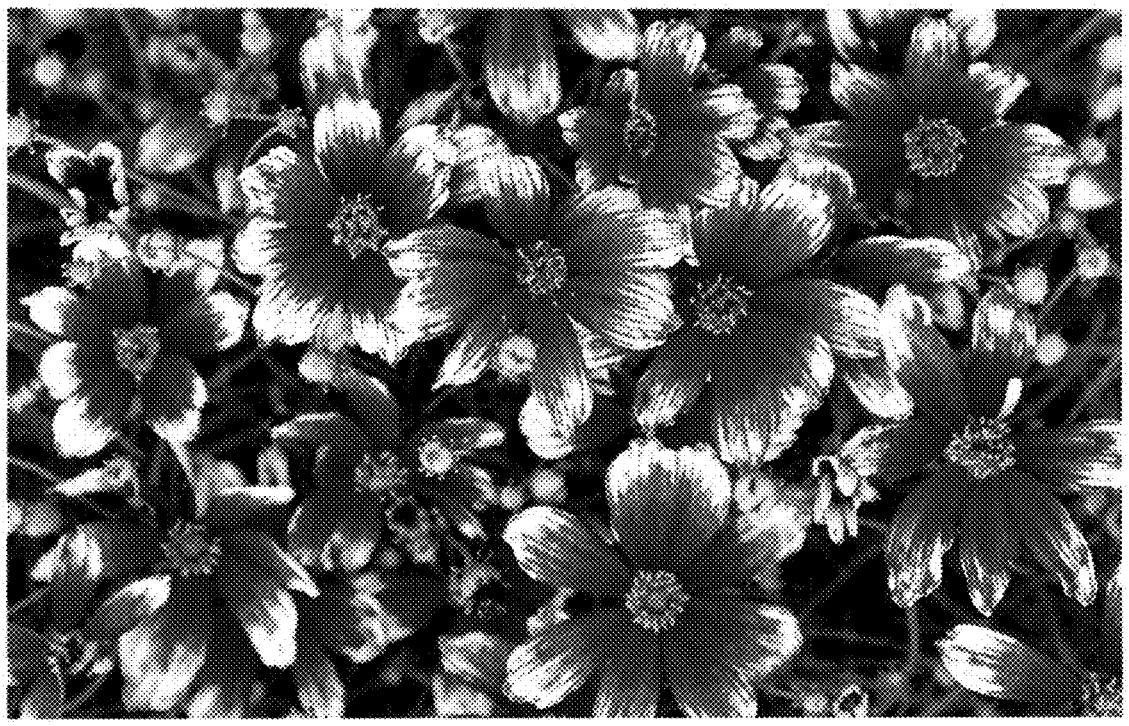
FIG. 2 shows a close-up of the flowers and buds of the new plant.

The following description is based on a three-year-old plant growing in a full-sun trial garden in Zeeland, MI, USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent 'Hot Paprika'; male or pollen parent was 16-22-x.

Asexual propagation: Cuttings, about 10 to 14 days to initiate roots; time to finish as #1 field grown size about 9 months.

Plant habit: Dense axillary branches; rounded, herbaceous perennial mound; up to 46 cm wide and 35 cm tall; average about 40 cm across and 31 cm tall.

Branches: Up to 10 per stem, lower branches compound; glabrous, cylindrical; to 23 cm long and 2 mm diameter; emerging at an angle about 45 degrees above horizontal.

Branch color: Between RHS 137A and RHS 138A, with some random blush of nearest RHS 187A.

Leaves: Opposite; entire; variable, linear to irregularly tri-lobed or penta-lobed, deeply dissected to midrib; acute apex; base attenuate; sessile; glabrous.

Leaf size: Up to 8.2 cm long and 9.8 cm wide, average about 5.8 cm long and 6.0 cm wide; side lobes at about a 45° to 60° angle to center lobe, center lobe to 5.2 cm long and 2 mm across.

Leaf color: Young expanding leaves adaxial nearest RHS 146A and abaxial nearest RHS 146D; mature leaves adaxial between RHS NN137A and RHS 137A, abaxial nearest RHS 137B.

Veins: Pinnate; only abaxial midrib obvious.

Midrib color: Adaxial nearest RHS NN137A, abaxial nearest RHS 137A.

Inflorescence: Radiate; composite, consisting of a single row of ray and inner disk florets; on terminal branches; about 5.6 cm diameter, about 1.2 cm tall from lower involucral bracts to top of disk florets; attitude upright to outwardly; to about 50 inflorescences per stem.

Flower fragrance: None detected.

Phyllary: Two distinct whorls; an outer or lower set consisting of about eight, lanceolate, salient, glabrous adaxial and abaxial, with acute apex and truncate base, to about 4 mm long and 1 mm wide at base; an inner or upper set pressed tight against ray florets, usually eight in number, to about 7 mm long and about 3 mm wide, ovate, acute apex and rounded base.

Phyllary color: Lower set between RHS NN137A and RHS 137A both adaxial and abaxial; upper set between RHS 137A and RHS 146A in the proximal and central portion of both adaxial and abaxial, marginally and distally nearest RHS N144A both adaxial and abaxial.

Flowering period: Early summer until late summer, for about 10 weeks.

Flower longevity: 4 to 6 days on the plant or as a cut flower.

Inflorescence buds: One to two days before ray floret flattening—terete; flat top and rounded base; 6.5 mm wide and 16 mm tall.

Inflorescence bud color: Exposed ray florets between RHS 160A and RHS 11B with proximal undertones nearest RHS 187A.

Peduncle: Cylindrical; glaucous; upright attitude; thin, wiry, stiff, strong; to about 1 mm diameter at the base and about 8 cm long before capitulum; about 8 ray florets and 40 to 45 disk florets per peduncle.

Peduncle color: Nearest RHS 137A.

Stem: Cylindrical; glabrous; with about six nodes, average internode spacing about 6 cm; spacing increasing distally.

Stem color: Proximally nearest RHS 137A with moderate blush in random areas nearest RHS 187A; distally, between RHS 137A and RHS 138A, with some random blush of nearest RHS 187A.

Node: Swollen to about 5 mm across.

Node color: As surround stem, nearest RHS 137B.

Bristles: Thin; lustrous; about 7 mm long and 0.5 mm across; color nearest RHS 17C.

Ray florets: Imperfect; sterile; zygomorphic; typically, 8 per inflorescence.

Ray floret ligule: Oblong elongate; glabrous adaxial and adaxial; apex typically two-notched; margin entire; base claw, narrowly cuneate to attenuate; opening flat to form 180° angle with other ray florets; parallel-veined; to about 28 mm long and about 13 mm wide; basal corolla claw about 2 mm long and about 0.7 mm diameter.

Ray floret color: Adaxial and abaxial basal 2 mm claw nearest RHS 151C; when first opening proximal two-thirds to three-quarters adaxial between RHS 187A and RHS 187B, with distal one-third to one-quarter margin nearest RHS 4C; when first opening abaxial proximal one-third eye zone nearest RHS N186D with a faint overtone of nearest RHS 163B, center one half nearest RHS 163B and distal one-quarter margin nearest RHS 4D; when mature, adaxial proximal one-third to one-quarter nearest RHS N186D with slight overtone on margin and heavy overtone in center of nearest RHS 159A, middle portion nearest RHS 159A with heavy undertone of nearest RHS N186D, and distally along margins nearest RHS NN155A; adaxial veins transition from between RHS 187A and RHS 187B initially to between RHS 59A and RHS distally lightening in the center to nearest RHS N186D when mature, and distal one-third to one-quarter of margin lightening to nearest RHS NN155B; abaxial major veins upon first opening and when mature nearest RHS N144A.

Disk florets: About 42 to 50 per capitulum; consisting of tepals, staminal tube, and pistil; size about 10 mm long by 1 mm wide at apex and about 0.7 mm diameter at base.

*Tepals.*—Four; 4 mm long and 1 mm wide, corolla fused in the basal 3 mm, acute apex.

*Tepal color.*—Adaxial nearest RHS 187B in distal 1 mm, abaxial distal 1 mm between RHS 165A and RHS 165B, basal 2 mm nearest RHS 15D, and middle portion between RHS 165B and RHS 164B.

*Staminal tube.*—Made up of four fused anthers; about 2.5 mm long and 0.5 mm diameter.

*Anther.*—About 2.5 mm long; color nearest RHS N186A.

*Filaments.*—Four; cylindrical; about 1.5 mm long and 0.1 mm diameter; color nearest RHS 13B.

*Pollen.*—Abundant; minute; color nearest RHS 15A.

*Style.*—Cylindrical; about 7 mm long and 0.2 mm diameter; color nearest RHS 17C.

*Stigma.*—Bifid and reflexed as it matures; about 1 mm long and 0.3 mm diameter; color nearest RHS 15B.

Seed: has not been observed: *Coreopsis verticillata* 'Heartstrings' is tolerant of winter temperatures as low as −20° C. and summer temperatures as high as 40° C. Once established it is also tolerant of dry summer conditions but does best with ample moisture and good drainage. It is not known to be tolerant or susceptible to diseases and pests that are common to other *Coreopsis* cultivars.

I claim:

1. A new and distinct cultivar of *Coreopsis* plant named 'Heartstrings' as described and illustrated.

* * * * *